United States Patent [19]

Snyder et al.

[11] Patent Number: 5,023,061
[45] Date of Patent: Jun. 11, 1991

[54] CHROMATOGRAPHIC SEPARATION OF ZIRCONIUM ISOTOPES WITH ANHYDROUS READILY RECYCLABLE ELUENTS

[75] Inventors: Thomas S. Snyder, Oakmont, Pa.; Ernest D. Lee, Ogden, Utah

[73] Assignee: Westinghouse Electric Corp., Pittsburgh, Pa.

[21] Appl. No.: 546,982

[22] Filed: Jul. 2, 1990

[51] Int. Cl.$^5$ .................. B01D 15/08; C22B 34/14; C10G 25/00; C10G 27/00
[52] U.S. Cl. .................................. 423/70; 423/2; 423/69; 423/73
[58] Field of Search .................. 423/69, 70, 73, 74, 423/2

[56] References Cited

U.S. PATENT DOCUMENTS

| | | | |
|---|---|---|---|
| 2,546,953 | 3/1951 | Street, Jr. | 423/70 |
| 2,571,237 | 10/1961 | Hansen | 423/70 |
| 2,753,250 | 7/1956 | Wilhelm et al. | 423/70 |
| 2,759,793 | 8/1956 | Lister et al. | 423/70 |
| 3,891,413 | 6/1975 | Sievers et al. | 55/67 |
| 3,960,762 | 6/1976 | Kroebel et al. | 252/426 |
| 3,971,842 | 7/1976 | Ewbank | 423/7 |
| 4,584,183 | 4/1986 | Chiang et al. | 423/2 |
| 4,711,768 | 12/1987 | Peterson et al. | 423/21.5 |
| 4,767,513 | 8/1988 | Peterson et al. | 204/157.21 |

FOREIGN PATENT DOCUMENTS 800426 8/1958 United Kingdom ............... 423/70

OTHER PUBLICATIONS

Byers et al., "Pilot-Scale Studies of Sugar Separations by Continuous Chromatography", Oak Ridge National Laboratory, pp. 1-29.

Primary Examiner—Richard D. Lovering
Assistant Examiner—Greg M. Sweet

[57] ABSTRACT

The isotopes of zirconium can be partially or completely separated by loading an essentially anhydrous alcoholic solution of an ionic compound of zirconium onto a cationic exchange resin with pentavalent phosphorus derived active groups which serves as the stationary phase of a chromatograph, eluting the compound with an essentially anhydrous alcoholic solution of hydrogen chloride and collecting distinct elution volumes representative of each isotope. In a preferred embodiment, the active groups of the cation exchange resin are derived from di-2-ethylhexyl phosphoric acid, tri-n-octyl phosphine oxide or tributyl phosphate and the chromatograph is of a type, such as a continuous annular chromatograph that it can be operated in a continuous steady state manner.

22 Claims, 5 Drawing Sheets

CHROMATOGRAPHIC SEPARATION OF ZIRCONIUM ISOTOPES WITH ANHYDROUS READILY RECYCLABLE ELUENTS

FIELD OF THE INVENTION

The present invention is concerned with processing zirconium to obtain a lower average thermal neutron capture cross section by a partial or complete separation of its isotopes thus improving its suitability as an internal material of construction for a nuclear reactor, for instance, as a fuel rod cladding.

BACKGROUND OF THE INVENTION

Zirconium metal has historically been a material of construction, in particular cladding for fuel rods, for nuclear reactors, and there has been a continuing interest in reducing its tendency to adsorb thermal neutrons. The more transparent the internal materials of construction of a nuclear reactor are to such thermal neutrons the more efficiently the reactor will function since a certain number of these neutrons are necessary to sustain the nuclear reaction and their production must compensate for the adsorption by the internal materials of construction. Early efforts were directed to separating zirconium from hafnium. The two elements occur together naturally but the hafnium has a substantially larger capture section for thermal neutrons. Such efforts involved both chromatographic techniques using an ion exchange resin and various solvent extraction techniques.

Recent efforts have been directed to isolating a zirconium isotope with either a particularly high or a particularly low cross section to thermal neutrons. This allows the production of a zirconium with a lower average cross section than one composed of the naturally occurring isotope distribution. These efforts at isomer separation have generally involved some type of solvent extraction. These separation techniques are generally only able to separate one isomer at a time. Thus they do not provide a means for simultaneously isolating the zirconium 90 and 94 isotopes which are recognized as having particularly small cross sections (one source lists them as 0.055 and 0.031 Barns, respectively, as compared to 0.567 Barns for zirconium 91 and 0.1430 for zirconium 92).

More recently, it has been proposed that isotopes of zirconium could be separated in an economically practical manner by the use of continuous steady state chromatography utilizing a cation exchange resin as the stationary phase. The preferred stationary phase in this proposal was sulfonated crosslinked polystyrene beads. It appears that this proposal provides a continuous process for isolating both of the abundant low thermal cross section isotopes, zirconium 90 and zirconium 94, in a single procedure.

It is an object of the present invention to provide an improved process for chromatographically separating the isotopes of zirconium. It is a further object of the present invention to provide a process which facilitates the recycle of the eluant. It is an additional object to provide a process which facilitates the concentration of heavy metal waste and radiochemical waste and also facilitates the separation of these two types of waste from each other. Another object of the present invention is to provide a process which facilitates converting the high thermal neutron capture cross section isotopes to high quality ceramic material.

SUMMARY OF THE INVENTION

A process for the partial or complete separation of the isotopes of zirconium using chromatography has been developed in which a cation exchange resin with active groups derived from pentavalent phosphorus is the stationary phase, an essentially anhydrous alcoholic solution of an ionic compound of a mixture of zirconium isotopes is the feed, and an essentially anhydrous alcoholic solution of hydrogen chloride is the mobile phase. The process involves the mobile phase eluting the zirconium isotopic solute, under conditions such that each of the various naturally occurring isotopes of zirconium is primarily eluted in an elution volume distinct from the elution volumes of the other isotopes. In a preferred embodiment the conditions are such that at least one of the elution volumes contains essentially only one isotope of zirconium. The process is preferably conducted in a steady state, continuous manner, and it is particularly preferred to conduct it in a continuous annular chromatograph.

A particular preferred embodiment involves feeding zirconium chloride dissolved in a one to five carbon alkanol to a continuous annular chromatograph with a stationary phase which comprises a cation exchange resin with active groups derived from pentavalent phosphorus. The mobile phase for the elution is preferably an essentially anhydrous methanol or ethanol solution of hydrogen chloride.

DETAILED DESCRIPTION OF THE INVENTION

Figure 1:
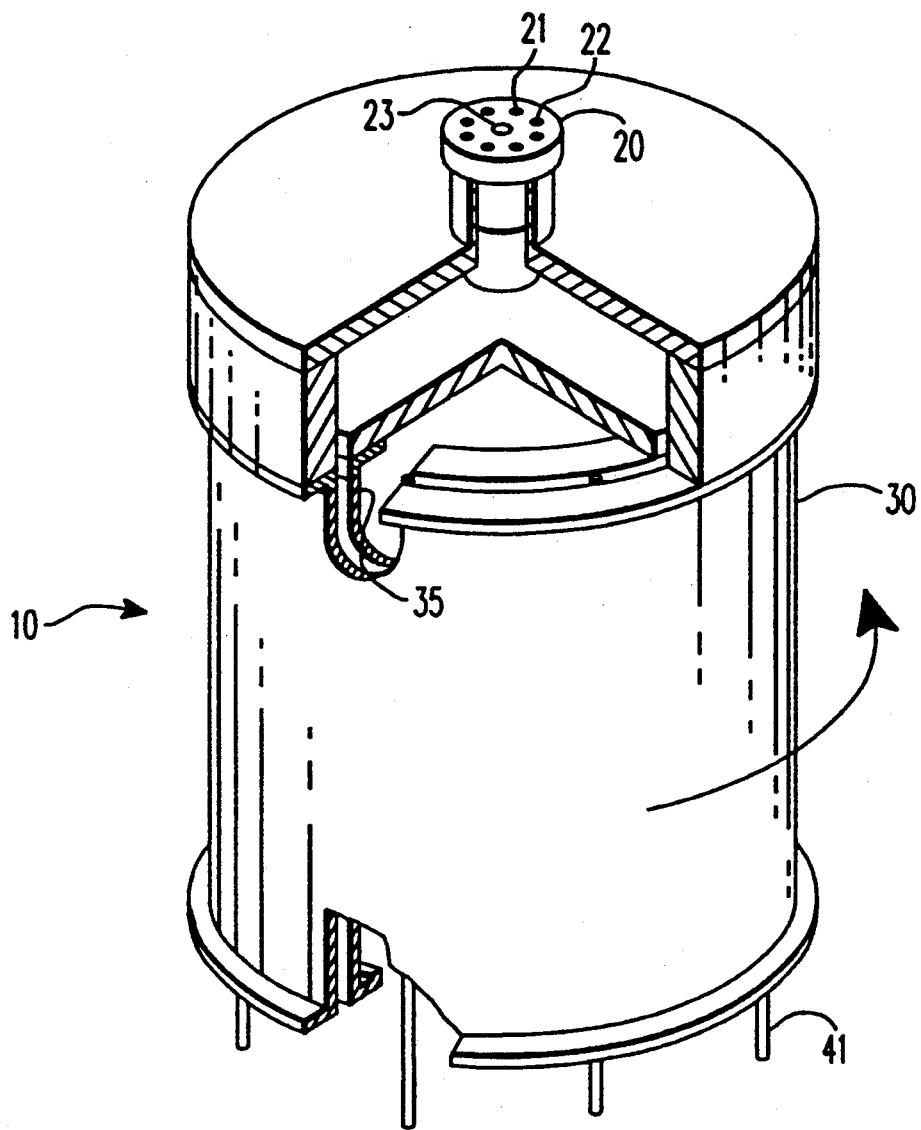
FIG. 1 is a perspective view of a continuous annular chromatograph (CAC) with a portion in section to illustrate the annular construction.
Figure 2:
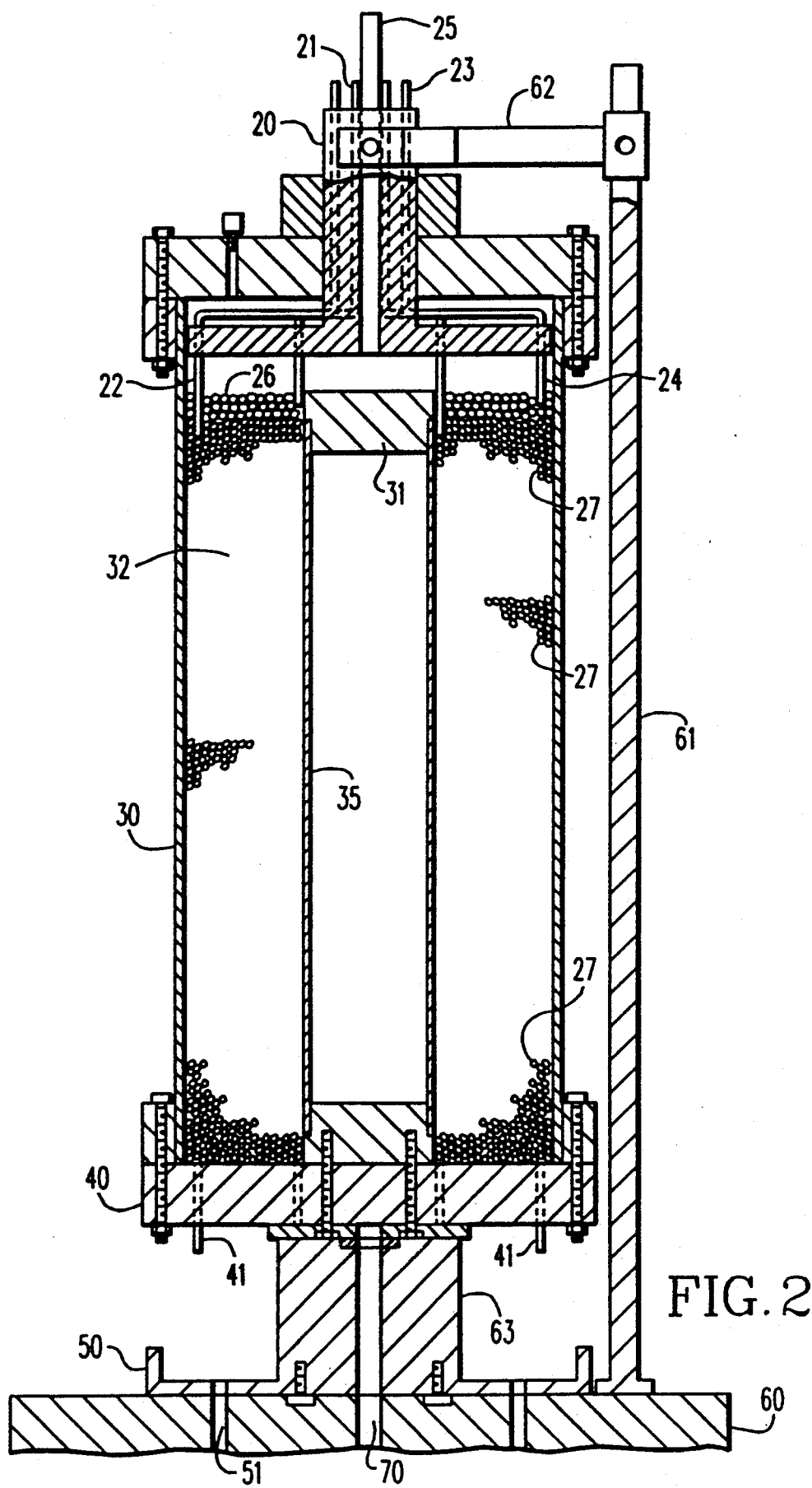
FIG. 2 is a horizontal sectional view of the CAC along a diameter of the concentric circles defining the annulus.
Figure 3:
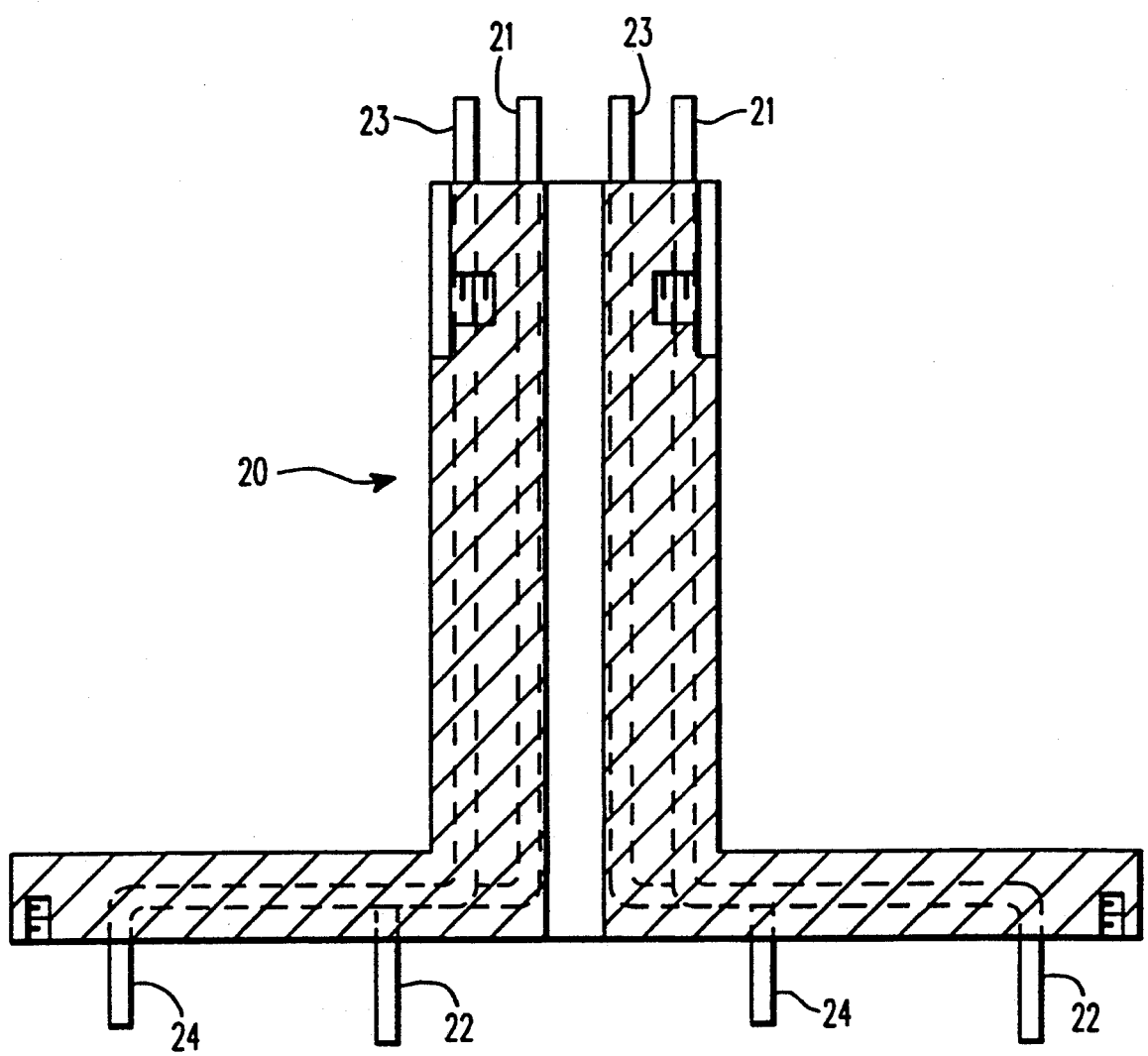
FIG. 3 is an enlarged horizontal sectional view of a part of the top portion of the CAC.
Figure 4:
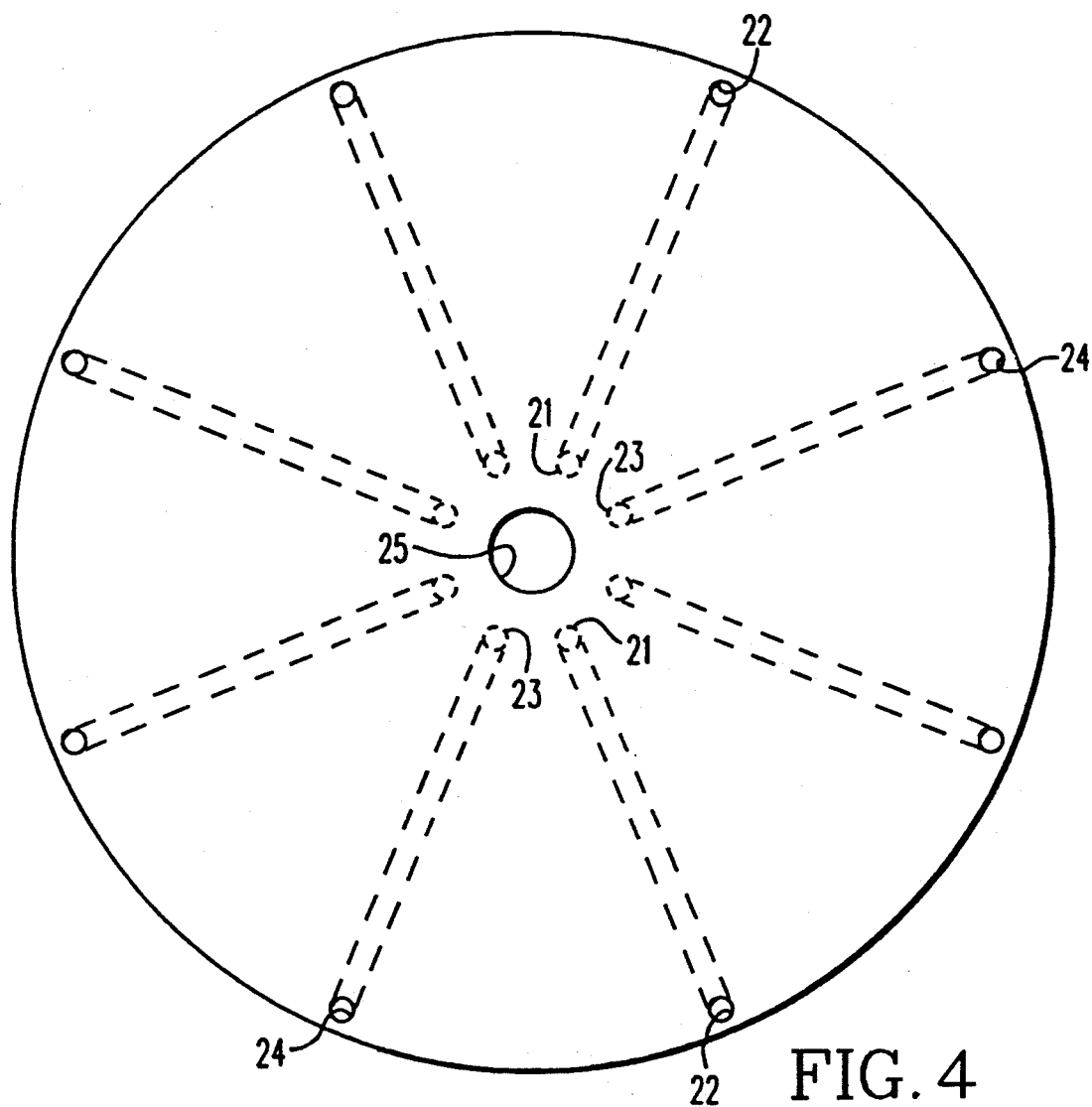
FIG. 4 is a plan view of the bottom of the item shown in FIG. 3.

The stationary phase can be any cation exchange resin with active groups derived from pentavalent phosphorus which have a propensity to complex with the zirconium compounds present in an alcoholic solution of zirconium tetrachloride. Typically present in such solutions are $ZrCl_3OR$ and $ZrCl_2(OR)_2$ wherein R is a $C_1$ to $C_5$ alkyl. It is preferred that the exchange resin display a very strong unit tendency to form such complexes. It is particularly preferred to utilize cation exchange resins with the highest capacities possible—typically between about 0.01 and 0.5 milliequivalents per milliliter with a most probable capacity of about 0.1 milliequivalents per milliliter under elution conditions. A particularly preferred and convenient range of complexing capacity is between about 0.01 and 0.1 milliequivalents per milliliter.

It is also preferred that the stationary phase comprise a narrow monodisperse distribution of spherical particles with a small average particle size. Deviations in particle size make it more difficult to get efficient separation. Thus, a polydisperse particle size distribution will require a longer column length and result in more dilute product fractions because a larger range of eluent volumes will contain desired product. The separation efficiency can also be enhanced by narrowing the particle size range of a monodisperse distribution. A small particle size is preferred because the exchange reaction is a phenomenum which occurs at the surface of the resin beads of the stationary phase. Thus, separation efficiency is enhanced by maximizing the surface to volume ration of these resin beads. However, this needs to be balanced by the effect which decreasing the particle size has on the permeability of the stationary phase. In general, an average particle size less than about 125 microns is preferred with a particle size less than about 25 microns being more preferred and a particle size less than about 10 microns being especially preferred. A particle size of one micron is optimum for separation efficiency but may pose problems of insufficient permeability for economically desired flow rates and problems of how to retain the beads in the column.

An especially preferred stationary phase comprises resin beads carrying active groups derived from tri-n-octyl phosphine oxide, tributyl phosphate or di-2-ethylhexyl phosphoric acid, especially the last of these.

The feed phase may be any convenient solution of ionic zirconium compounds formed from a mixture of zirconium isotopes. The isotope mixture may be that which occurs in nature or it may be a partially refined mixture obtained from a preliminary refinement process.

A preferred feed phase is that obtained from dissolving zirconium tetrachloride in an essentially anhydrous one to five carbon alcohol. Crude zirconium is commercially obtained by chlorinating zircon sand in the presence of coke at about 1000° C. and separating the resulting zirconium tetrachloride from the resulting silicon tetrachloride by means of a differential condenser. The zirconium fraction typically contains a natural distribution of isotopes and also contains hafnium tetrachloride. Both compounds are readily dissolved to yield an essentially anhydrous alcoholic solution suitable for use in a chromatographic process. It is particularly preferred to use methanol or ethanol as the solvent.

It is preferred that the feed phase be as concentrated as possible without an undue risk of exceeding the solubility limit for the solute during the course of the process. In the preferred feed phases, the solubility limit is somewhat in excess of 233 g/l of zirconium tetrachloride. A convenient concentration is between about 0.5 and 1 molar zirconium with a particular preference for about 1 molar zirconium. A metal concentration of less than about 0.3 molar is likely to result in an economically unattractive process.

The mobile phase may be a between about 1 and 6 molar, preferably between 1 and 4 molar, and most preferably a between about 1 and 3 molar solution of hydrogen chloride in any essentially anhydrous alcohol which has a low enough viscosity to be useful in chromatography, is free of any chemical groups other than hydroxyls likely to be reactive under the processing conditions and has a dielectric constant which permits the zirconium compounds present to complex with the active groups of the cation exchange resin. The between one and five carbon alkanols are preferred and ethanol and methanol are particularly preferred.

Both the feed phase solution and the mobile phase solution may contain water up to the azeotropic limit for that particular solution. For the purposes of this disclosure, solutions with water up to this limit are considered to be essentially anhydrous.

The effective column height should be sufficient to allow significant resolution of the various isotopes of zirconium into distinct product fractions. The resolution is preferably sufficient to yield an isotope purity in excess of about 90 percent, more preferably at least about 98 percent. It is preferred that this resolution be effected in a single pass through the column. The effective column height needed for a given resolution can be estimated from an application of the Kremser-Brown-Sounders equation, to empirical data on the separation capacity of a given stationary phase, mobile phase, eluent and flow conditions.

An inherent result of a resolution of the isotopes of zirconium is an efficient separation of hafnium from zirconium. A process sufficiently sensitive to separate isotopes of zirconium will readily effect a separation of hafnium. In this regard, in this anhydrous eluent system in the above-disclosed hydrogen chloride concentrations, hafnium binds much more tightly to the cation exchange resin than zirconium. Comparative affinity data from solvent extraction work shows that with proper adjustment better than an order of magnitude of differences in affinity should be achievable.

Thus, it is possible to use elution conditions which leave the hafnium bound to the cation exchange resin during the steady state operation of the chromatograph. It can then be displaced from the stationary phase in a batch operation between campaigns of steady state operation. The relatively low concentration of hafnium in typical zirconium feedstock (between about 10 and 20 mol percent in chlorinated zircon sand) allows a substantial period of steady state operation before the capacity of the cation exchange resin is significantly adversely effected.

A separation factor, $\alpha$, is used to define the ability to separate the zirconium isotopes. This factor is itself defined by the following formula for the binary case:

$$\alpha = \frac{y/(1-y)}{x/(1-x)} \qquad (1)$$

wherein y is the molar concentrations of the desired isotope in the product faction rich in that isotope and x is the molar concentration of this same isotope in the tails fraction. Approximate calculations can be performed by selecting one isotopic fraction as the product, and defining the tails fraction as the composite of the other product fractions. Thus, if a product fraction is obtained in which 98% of the zirconium is zirconium 90 and if in the composite of all the other product fractions together only 2% of the zirconium is zirconium 90, the $\alpha$ defining this separation would be $$\frac{0.98/(1-0.98)}{0.02/(1-0.02)} = 2401$$

Separation factors, $\alpha$, for isotopic separations are conveniently evaluated on 25 to 100 cm columns with the 25 cm length being preferred. For such columns $\alpha$ values for zirconium 90 on the preferred stationary phases with the preferred eluents are greater than about 1.05, preferably greater than about 1.085.

The use of cation exchange resins with pentavalent phosphorus derived active groups, especially those derived from the three particularly enumerated phosphorus compounds, greatly facilitates the attainment of high α values. Such active groups have a particularly strong affinity for zirconium cations as evidenced by solvent extraction data. The stronger the interaction between the resin and the zirconium cations, the better will be the resolution between the various isotopes. This can be analogized to a foot race. The more difficult the course, the easier it is to separate the better runners from the rest of the pack. Thus, the use of these cation exchange resins allows the use of shorter columns to effect the same degree of resolution.

The effective column length required for any desired degree of purification is then determined from this data. For instance, if a 25 cm test column yields a separation factor, α, of 1.085 this can be used as the separation factor for a theoretical stage, $α_s$, in applying the Kremser-Brown-Sounders equation in estimating the number of theoretical stages, N, required. This formula can be used in the form:

$$N = \frac{\ln α_T}{\ln α_S}$$

For the case being discussed this yields the following result:

$$N = \frac{\ln 2401}{\ln 1.085} = 95.4$$

Thus, 95.4 theoretical stages of 25 cm each are required which implies an effective column length of about 24M.

The following table shows projected column length as a function of α and desired product purity. It is based on the assumption that the Kremser-Brown Saunders equation holds in the Underwood-Fenske form assuming the binary mixture approximation:

| α for 0.25 M Test Column | 98% Purity | | 95% Purity | |
|---|---|---|---|---|
| | Number of Stages | Total Column Length (M) | Number of Stages | Total Column Length (M) |
| 1.001 | 7830 | 1960 | 4970 | 1744 |
| 1.01 | 786 | 200 | 500 | 175 |
| 1.03 | 265 | 66 | 168 | 42 |
| 1.09 | 102 | 26 | 65 | 16 |
| 1.1 | 82 | 21 | 52 | 13 |

The effective column height can be vertical but it may have other orientations. What is important is the effective path over which the mobile phase travels.

It is preferred that the path be provided in such a way that the chromatographic separation can be operated continuously. There is no convenient technique currently available for instantaneously sensing the concentration of any given isotope of zirconium. Thus, there is a preference for a continuously operating procedure which has reached steady state so that a particular product fraction reproducibly has a certain isotope distribution. If the chromatographic separation is effected in a discontinuous or batch manner random variations between runs may make it difficult to reproducibly collect product fractions with the same isotope distributions from run to run. For instance, if a single vertical column is loaded in a batch manner the elution time of the product fraction rich in a particular isotope may vary from run to run due to random variables difficult to control such as feed concentration fluctuations, etc.

A particularly preferred continuously operating chromatograph is the continuous annular chromatograph. This device was developed by Oak Ridge National Laboratory and comprises an annular stationary phase which is rotated about the axis of the annulus. The annulus is provided by packing the stationary phase material, such as resin beads, between two concentric cylinders of differing diameters with vertical axes. A feed port is provided at a given angular position and one or more eluent ports are provided at some angular offset from the feed port. It is preferred to place a layer of glass beads above the stationary phase, and to feed the eluent to the glass beads while feeding the zirconium feedstock directly to the top of the stationary phase. This should prevent any undesired mixing effects.

This device is provided with a number of product ports set at a number of angular positions which can be set arbitrarily to accommodate a particular set of operating condition. Each product port collects an elution volume which has had a particular residence time on the column. The stationary phase is typically rotated at a constant speed so that any vertical segment of the annular bed is above a particular fixed product collection port at a given time after this segment has been loaded with zirconium feedstock and eluent. Thus, the angular position of each product collection port corresponds to a particular elution time for a particular rate of rotation of the stationary phase and for a particular flow rate through the stationary phase. While the stationary phase rotates above the product collection ports, they are arranged such that every elution volume is collected at particular collection port or group of collection ports.

The flow rate through the stationary phase is controlled by the pressure drop across the effective height of the stationary phase and the physical characteristics of the stationary phase, i.e., particle size and packing void volume. This pressure drop may be provided by the hydrostatic head of the feedstock and eluent but it is preferably provided by pressurizing the device. The pressure required to achieve a particular flow rate is governed by the nature of the stationary phase; the smaller the average particle of the resin beads making up the stationary phase the larger the pressure drop required to obtain a particular flow rate over a particular effective height. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

The flow rate across the effective height of the stationary phase and the rotational speed of the stationary phase should be coordinated such that a particular product fraction always elutes at the same angular position and thus is always delivered to the same product collection port.

It is preferred that the chromatograph be operated in a displacement mode wherein no more than about 5 percent, more preferably no more than about 1 percent of the effective column height, is loaded with feed solution before the zirconium species is eluted or displaced down the column. This is conveniently effected by using a feed solution which has insufficient acid strength to release the zirconium complexes from bonding with the cation exchange resin and loading no more than about 5 percent, preferably about 1 percent of the effective height, before adding an eluent of sufficient strength to cause the zirconium species to migrate down the column at a reasonable rate. In the continuous annular chromatograph this end is achieved by coordinating the angular displacement between the feed port and the eluent port and the speed of rotation of the annular bed so that the time interval between loading and elution is just sufficient for the desired degree of penetration. The relationship between the time for loading and the depth of penetration is in turn governed by the flow rate through the annular bed.

The elution displacement process may be effected by employing either an isocratic or a gradient mode of supplying eluent. In the former case, the eluent can simply be supplied from a single port while in the latter case, several ports at successively greater angular displacements from the feed port are utilized. In the gradient mode, elution under the influence of the initial eluent is permitted to proceed until some separation of the zirconium isotopes has been effected and then eluent with a higher hydrogen chloride concentration is supplied. This increases the migration speed of the zirconium cations down the column and minimizes the range of elution volumes or times over which a given component or product fraction will exit the column or, in other words, this procedure minimizes the band spreading.

Decreasing the elution volumes by gradient elution or by other means increases the concentration of the product, i.e., the zirconium isotope, in the product fraction. Concentrations greater than about 5 g/l, especially between about 20 and 40 g/l, and more especially between about 50 and 70 g/l are preferred. In this regard, the ability to practice gradient elution may be limited by the solubility of hydrogen chloride in some alcohols. Thus, the range of concentrations over which a gradient can be constructed may be fairly narrow.

The flow rate down the column is governed by the pressure drop from the top to the bottom of the column and the nature of the stationary phase. The smaller the average particle size of the resin beads making up the stationary phase the higher the pressure drop required to obtain a given flow rate. This relationship is also effected by the particle size distribution of these resin beads. There is, however, a maximum attainable flow rate for any given cation exchange resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 20 and 80, more preferably between about 30 and 50 gallons per minute per square foot of cross sectional area (between about $1.36 \times 10^{-2}$ and $5.43 \times 10^{-2}$ m³/sec, more preferably between about $2.04 \times 10^{-2}$ and $3.40 \times 10^{-2}$ m³/sec per square meter of cross sectional area) There is a relationship between the achievable flow rates and the effective column height needed for a given degree of purity. For a given system of stationary phase and eluent, the theoretical stage separation factor, $a_s$, of the stationary phase will increase as the average particle size of the resin beads of the stationary phase decrease. However, as this particle size decreases so does the flow capacity of the stationary phase. Thus, there is an inverse relationship between $a_s$ and the flow capacity. Thus, a higher flow rate will require a greater effective column height to achieve the same degree of separation or product fraction purity.

Furthermore, there is the additional constraint that the pressure required to achieve the desired flow rate not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and consequently its theoretical stage separation factor, $a_s$, is decreased, the required effective height and the required overall pressure drop are both increased. On the other hand, as the theoretical stage separation factor, $a_s$, is increased by a change in the resin bead size distribution and consequently the flow capacity of the stationary phase is decreased, the pressure drop for a given effective height is increased. A pressure drop of less than about 2758 kPa (400 psi) more especially between about 345 and 1042 kPa (50 and 150 psi) is preferred.

Thus, to obtain a system with a commercially practical capacity, it is necessary to use a stationary phase which will simultaneously display both a reasonable theoretical stage factor, $a_s$, and a reasonable flow rate per unit of effective height with a reasonable pressure drop. This can be achieved by an appropriate selection of both the complexing capacity of the stationary phase cation exchange resin and the eluent.

In a preferred mode several product collection ports are used to collect a particular product fraction. This is accomplished by closely spacing these collection ports so that they more than span the angular range of rotation that corresponds to the elution time interval of that particular fraction but do not extend to angular positions at which any significant portion of any other product fraction is expected to elute. Of course, this requires that the elution time intervals of different product fractions do not substantially overlap. This arrangement tends to insure that minor fluctuations in the steady state elution behavior which would cause a slight advancement or retardation of the elution time of the desired product fraction will not result in any loss of this fraction.

A particular preferred device for use in practicing the present invention is illustrated in FIGS. 1 through 5. The continuous annular chromatograph 10 illustrated in FIG. 1 comprises two concentric cylinders 30 and 35 which define the annular space 32 seen in FIG. 2. Atop this annular space 32 is a distributor plate 20. Feed pipes or channels 21 and 23 run through the distributor plate 20 and terminate in feed nozzles 22 and 24, respectively. The feed nozzles 22 are intended to supply the feed phase to the exchange resin beads 27 which are packed in the annular space 32. For ease of illustration, these beads are shown as only partially filling the annular space 32. On the other hand, the feed nozzles 24 are intended to feed the eluent to the layer of glass beads 26 which sits atop the exchange resin beads 27. Thus the feed nozzles 24 are somewhat shorter than the feed nozzles 22. This feed arrangement serves to avoid any back mixing of the feed phase.

The central cavity defined by the inner cylinder 35 is sealed by a cap 31 so that pipe or channel 25 can be used to apply pressure to the annular bed of resin beads 22.

Figure 5:
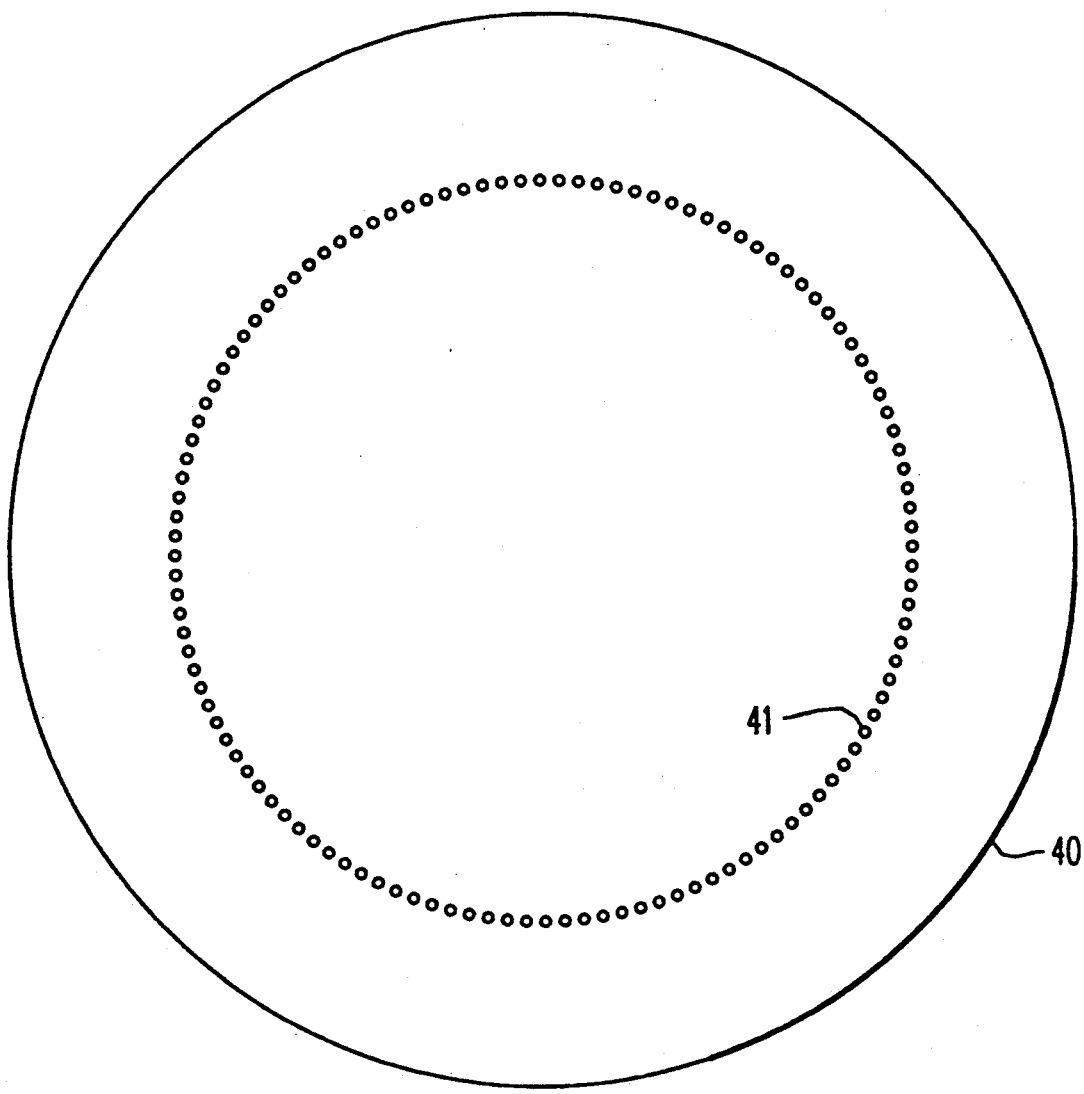
FIG. 5 is a plan view of the bottom of the CAC.

The bottom of the annular space 32 is defined by a product plate 40. As seen in FIG. 5, a large number of product delivery channels or pipes 41 pass through this plate. This allows the collection of a variety of product fractions and also facilitates adjustments to the operating conditions to allow product collection at various angular displacements.

The distributor plate 20 is held in a fixed position above the annular space 32 by a bracket 62 which is turn connected to a support rod 61 which is affixed to a base plate 60. Also affixed to this base plate 60 is a support column 63 on which the product plate 40 rotatably rests. A shaft 70 passes through this support column 63 and base plate 60 and connects the product plate 40 to a motivating means not shown. Also affixed to the base plate 60 is an annular collection trough 50 which can be subdivided into any number of convenient segments, each with its own exit port 51.

The continuous annular chromatograph 10 is operated by rotating the annular space 32 packed with the resin beads 27 beneath the fixed distributor plate 20 and its associated feed nozzles 22 and 24. The rotational force is supplied by the shaft 70.

We claim:

1. A process for reducing the thermal neutron cross-section of zirconium by increasing the concentration of the low cross-section isotopes and decreasing the concentration of the high cross-section isotopes which comprises subjecting an essentially anhydrous alcoholic solution of an ionic zirconium compound with a higher than desired distribution of high cross-section isotopes to continuous steady state chromatography utilizing a cation exchange resin with pentavalent phosphorus derived active groups as the stationary phase, collecting at least two product fractions, one enriched in zirconium 90 and the other enriched in zirconium 94, and combining them to yield a zirconium with a lower cross-section than the starting zirconium.

2. The process of claim 1 wherein the concentration of the zirconium 90 in its product fraction is in excess of 90 mol percent.

3. The process of claim 1 wherein the continuous steady state chromatography is effected in a continuous annular chromatograph.

4. The process of claim 1 wherein the zirconium compound is a chloride.

5. The process of claim 1 wherein the active groups of the cation exchange resin are derived from one of the group consisting of tributyl phosphate, tri-n-octyl phosphine oxide, di-2-ethylhexyl phosphoric acid and combinations thereof.

6. The process of claim 1 wherein the eluent is a between 1 and 4 molar essentially anhydrous alcoholic solution of hydrogen chloride.

7. The process of claim 1 wherein the cation exchange resin has a capacity of between 0.01 and 0.5 milliequivalents per milliliter for complexing with the zirconium compounds present under the elution conditions.

8. The process of claim 7 wherein the cation exchange resin is composed of a monodisperse distribution of spherical beads with an average particle size of about twenty five microns or less.

9. The process of claim 1 wherein the separation factor, $\alpha$, for a theoretical stage of 25 cm in height for zirconium 90 is at least about 1.05 and the permeability of the stationary phase is such as to permit a flow rate of at least about 20 gallons per minute per square foot of cross section traverse to the flow.

10. The process of claim 1 in which the solution of the zirconium compound also contains a hafnium compound and the chromatography essentially completely separates the hafnium compound from the zirconium product fractions.

11. The process of claim 10 wherein the steady state conditions are such that the hafnium is retained on the stationary phase and is subsequently eluted in a separate operation.

12. A process for recovering a zirconium fraction with an enhanced concentration of the 90 and 94 isotopes comprising subjecting an essentially anhydrous alcoholic solution of an ionic zirconium compound with a natural isotope distribution to continuous steady state chromatography utilizing a cation exchange resin with a pentavalent phosphorus derived active groups as the stationary phase, collecting at least two product fractions, each enriched in one of these isotopes, and combining these two fractions.

13. A commercial process for obtaining zirconium with a reduced thermal neutron cross-section by increasing the concentration of the low cross-section isotopes and decreasing the concentration of the high cross-section isotopes which comprises
   1) preparing an essentially anhydrous alcoholic solution of zirconium tetrachloride with a natural isotope distribution to a solution strength of at least about one molar,
   2) subjecting this solution to continuous steady state chromatography in a continuous annular chromatograph wherein
      a) the eluent is a between about 1 and 4 molar essentially anhydrous alcoholic solution of hydrogen chloride,
      b) the stationary phase comprises a cation exchange resin which has
         i) pentavalent phosphorus derived active groups,
         ii) a capacity for complexing with the zirconium compounds present of between about 0.01 and 0.5 milliequivalents per milliliter under the elution conditions,
         iii) a monodisperse particle distribution of approximately spherical beads with an average particle size of about 25 microns or less, and
         iv) a separation factor, for zirconium 90 for a 25 cm theoretical stage of at least about 1.05, under the elution conditions,
      c) the effective height of the stationary phase is sufficient to yield a zirconium 90 product fraction which comprises 98 mol percent of zirconium 90, and
   3) collecting the two product fractions comprising mainly zirconium 90 and zirconium 94, respectively.

14. The process of claim 13 wherein the essentially anhydrous alcoholic zirconium chloride solution also contains hafnium chloride and the chromatography essentially completely separates the hafnium compound from the zirconium product fractions.

15. The process of claim 13 wherein the active groups of the cation exchange resin are derived from one of the group consisting of tributyl phosphate, tri-n-octyl phosphine oxide, di-2-ethylhexyl phosphoric acid and combinations thereof.

16. The process of claim 13 wherein the continuous annular chromatograph is operated so that the zirconium chloride solution penetrates about one percent of the effective column height before the eluent is added.

17. The process of claim 15 wherein the alcohol solvent comprises methanol or ethanol.

18. The process of claim 16 wherein the stationary phase has a capacity of about 0.1 milliequivalents per milliliter for complexing with the zirconium compounds present under elution conditions.

19. The process of claim 13 wherein the alcohol solvent comprises methanol or ethanol.

20. The process of claim 13 wherein the eluent is fed to the annular bed at more than one circumferential position and the hydrogen chloride concentration of the eluent is increased at each successive feed position moving in the direction of rotation of the continuous annular chromatograph.

21. The process of claim 13 wherein the flow rate is between about 20 and 80 gallons per minute per square foot of cross section traverse to the flow.

22. The process of claim 21 wherein the pressure drop across the effective height of the stationary phase is less than about 150 psi.

* * * * *